United States Patent [19]
Mauer et al.

[11] Patent Number: 4,654,271
[45] Date of Patent: Mar. 31, 1987

[54] METAL COMPLEXES USEFUL AS RUBBER/METAL BONDING PROMOTERS

[75] Inventors: Daniel E. Mauer, Grez-Doiceau; Philippe G. Moniotte, Heron, both of Belgium

[73] Assignee: Monsanto Europe, S. A., Brussels, Belgium

[21] Appl. No.: 719,855

[22] Filed: Apr. 4, 1985

[30] Foreign Application Priority Data

Apr. 10, 1984 [GB] United Kingdom ............... 8409245

[51] Int. Cl.$^4$ .................................................. B32B 15/06
[52] U.S. Cl. .................................... 428/465; 524/83; 556/139
[58] Field of Search ................. 428/461, 462, 465; 524/83; 556/139

[56] References Cited

U.S. PATENT DOCUMENTS

| | | | |
|---|---|---|---|
| 2,936,295 | 5/1960 | Brodkey et al. | 524/166 |
| 3,036,034 | 5/1962 | Rumscheidt | 524/166 |
| 3,535,249 | 10/1970 | Larson | 260/23 |
| 3,732,192 | 5/1973 | Arnold | 260/79.5 C |
| 3,869,435 | 5/1975 | Trivette | 260/79.5 C |
| 4,417,012 | 11/1983 | Moniotte | 524/83 |

FOREIGN PATENT DOCUMENTS 0109955 5/1984 European Pat. Off. .

OTHER PUBLICATIONS

A. S. Foust et al. article Inorg. Chem. 1980, 19, 1048–1050, "Preparation and Structure of the Bunte Salt Trans–Dichlorobis(Ethylenediamine) Cobalt (III) S-Hydroxymethyl Thiosulfate".

Primary Examiner—Edith Buffalow
Attorney, Agent, or Firm—Gordon B. Seward

[57] ABSTRACT

Compounds containing an organic thiosulphate anion and cationic nickel or cobalt in association with an amine, are useful in increasing the bond strength between metal, especially brass, and vulcanized rubber. Typical complexes are those where the anion is dodecylthiosulphate or hexamethylenebis(thiosulphate), and the amine is ethylenediamine or N-benzyl-N-t-octylamine.

14 Claims, No Drawings

METAL COMPLEXES USEFUL AS RUBBER/METAL BONDING PROMOTERS

This invention relates to the bonding of rubber to metal.

Articles in which rubber is bonded to metal have been known for many years, and since the introduction of the steel-belted radial tyre, rubber/metal bonding has been very extensively studied. It is known that certain substances will act as adhesion promoters to improve the initial adhesion level between the rubber and the metal and the maintenance of the adhesion level during accelerated laboratory ageing tests designed to simulate conditions to which the article may be subjected during its service life.

The main adhesion promoters currently used to promote the bonding of brass-coated steel to rubber are cobalt compounds, for example cobalt naphthenate, and resorcinol- and/or melamineformaldehyde resins used in conjunction with hydrated silica. Both of these types of adhesion promoters, which can be employed separately or in combination, have disadvantages, and alternative rubber/metal adhesion promoters to those currently employed are therefore desirable.

Our European Patent Application No. EP-A-O 109 955 discloses rubber/metal adhesion promoters that are metal salts of organic thiosulphates, including nickel and cobalt salts. Methods for the preparation of these salts are described in the said European Patent Application and also in No. EP-A-O 070 143. These salts tend to be at least moderately soluble in water and in water-miscible organic solvents, and because of this, their isolation after preparation by the above-referenced methods may involve evaporation of considerable quantities of water and/or solvents which is time- and energy-consuming.

The complexes used in the present invention are compounds containing an organic thiosulphate anion, and cationic nickel or cobalt in association with an amine. The complexes have rubber/metal adhesion promoter properties comparable with those of the nickel or cobalt thiosulphates referred to above, but in general they have considerably lower solubilities in water and water-miscible solvents, so that they can be prepared and isolated more efficiently.

The preparation of the salt trans-dichloro-bis(ethylenediamine)cobalt (III) S-hydroxymethyl thiosulphate is described by Foust and Janickis in Inorg. Chem. 1980, 19, 1048, but no uses for the salt are mentioned.

The invention includes a composite comprising a sulphur-vulcanisable rubber composition containing the rubber, sulphur, a vulcanisation accelerator, a complex as defined above and a component having a metal surface in contact with the composition.

A further aspect of the invention is an article in which a vulcanised rubber is bonded to a metal surface, especially a brass surface, the article having been obtained by heating a composite of the invention to a vulcanisation temperature to vulcanise the rubber.

Certain of the nickel and cobalt complexes useful according to the present invention are new compounds and are claimed as such.

The detailed structure of the complexes is not known with certainty in all instances. However, where the amine is one which is known to form a complex cation with divalent nickel or cobalt, it is believed that the metal and amine occur in the form of such a cation in the complexes of the invention. The complexes of the invention are usually hydrated, but can be anhydrous. Moreover, useful complexes include those where the metal is only partly complexed by an amine, other valencies being satisfied by the presence of, e.g. halogen or carbonyl.

Amines known to form complex cations with divalent nickel or cobalt include those of the general formulae $H_2N-R-NH_2$ where R represents a straight or branched chain group $C_nH_{2n}$, n having a value of from 2 to 8, generally from 2 to 6, with the amine groups being separated by a sequence of no more than 3 carbon atoms. Examples of such amines are 1,2-diaminoethane, 1,3-diaminopropane, 1,2-diamino-2-methylpropane, 1,3-diamino-2,2-dimethylpropane, 2,2-diaminobutane, and 2,3-diamino-2,3-dimethylbutane.

Also known as complex-forming amines are those having the above formula in which R represents a 1-phenylethylene or 1,2-diphenylethylene radical, or a radical of the formula $-CH_2CH_2NHCH_2CH_2-$. A further instance of an amine known to form a complex with nickel or cobalt is 2,2'-bipyridyl.

In other instances, complexes of the invention have been obtained from amines which are not known to form well-defined cationic complexes with cobalt or nickel. These amines include N-benzyl-N-(tert-alkyl)amines, where the tert-alkyl group has the formula

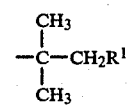

where $R^1$ represents H or a straight or branched-chain alkyl group of from 1 to 8 carbon atoms. Specific examples of such amines are N-benzyl-N-t-butylamine and N-benzyl-N-t-octylamine (i.e. N-benzyl-N-(1,1,3,3-tetramethylbutyl)amine).

Other amines which form complexes of the invention are poly(ethylene imines).

The thiosulphate anions in the complexes useful in the present invention normally contain one, two or three thiosulphate groups, and such anions can be represented by the formula $R^2(S_2O_3^-)_x$ where $R^2$ is an organic radical of valency x and x has a value of 1, 2 or 3. Many examples of such radicals are given in European Patent Application No. EP-A-O 109 955. More accurately, the anions would be described as S-ester thiosulphate anions, but are referred to herein as "organic thiosulphate" or "thiosulphate" anions for convenience.

When $R^2$ represents a monovalent radical, it is preferably a straight- or branched chain alkyl or alkenyl group containing up to 20 carbon atoms, more especially from 3 to 18 carbon atoms, or a benzyl or alkylbenzyl radical. Specific examples of such radicals are ethyl, n-propyl, isopropyl, allyl, sec-butyl, isoamyl, n-hexyl, hex-3-enyl, n-heptyl, n-octyl, 2-ethylhexyl, decyl, dodecyl, pentadecyl, hexadecyl, octadecyl, benzyl, 3-methylbenzyl and 3,5-dimethylbenzyl.

Representative of divalent radicals from which $R^2$ can be selected are straight- and branched chain alkylene radicals, preferably those containing 2 or from 5 to 16 carbon atoms, or analogous radicals containing from 4 to 16 carbon atoms and one or more double or triple bonds, for example alkylene or alkadienylene radicals. Examples of such radicals are ethylene, pentamethylene, hexamethylene, octamethylene, nonamethylene, decamethylene, dodecamethylene, 3-methyl-1,5-pentylene, 1,4-but-2-enylene, 1,6-hex-2-enylene and 1,8-octa-2,6-dienylene.

In other instances, a divalent radical $R^2$ has a structure comprising two or more alkylene units, each containing, for example, from 1 to 20 carbon atoms, pairs of such units being linked through an oxygen or sulphur atom, through a group $-SO_2-$, $-CO-$ or $-COO-$, or through an arylene or cycloalkylene radical. Representative of such structures are those of the formulae $-(CH_2)_a-O-(CH_2)_a-$
$-(CH_2)_a-O-(CH_2)_{a'}-O-(CH_2)_a-$
$-(CH_2)_b-CO-(CH_2)_b-$
$-(CH_2)_c-COO-(CH_2)_c-$
$-(CH_2)_c-COO-Y-COO-(CH_2)_c-$
and
$-(CH_2)_d-SO_2-(CH_2)_d-$ where each a, a' and c independently represents an integer of from 1 to 20, each b independently represents an integer of from 1 to 10, each d independently represents an integer of from 2 to 20, and Y represents a group $-(CH_2)_c-$ or a group $-(CH_2CH_2O)_eCH_2CH_2-$ where e represents an integer from 1 to 5. Preferred values for a are from 1 to 8, for example from 3 to 8, preferred values for a' are from 1 to 6, preferred values for b are 1 to 4, preferred values for c are from 1 to 18, for example from 3 to 12, and preferred values for d are from 2 to 12. Where values of a, a', c, d or e exceed 2, the alkylene radicals can be straight chain or branched.

Examples of radicals having a pair of alkylene units linked through an arylene radical are m-phenylene, p-phenylene, 1,4-naphthylene and 1,5-naphthylene.

Thiosulphate anions having three thiosulphate groups include those where three groups $-C_mH_{2m}-S_2O_3^-$, m typically having a value from 1 to 6, are substituents in an aromatic nucleus, for example a benzene or naphthalene nucleus, (which may also contain other substituents), or as substituents in one or more nuclei or a di- or tri-nuclear aromatic compound, for example biphenyl, diphenyl ether, diphenyl sulphone or benzophenone. Other examples are tri-N-substituted hexahydrotriazines where the substituent on each nitrogen atom is a group having the formula $-COC_mH_{2m}S_2O_3^-$. The most readily available of these hexahydrotriazines are compounds where m has the value 2.

The complexes of the invention can be formed by mixing in solution a source of nickel or cobalt ions, an alkali metal salt of an organic thiosulphate and an amine, and recovering the complex from the reaction mixture. The order in which the reactants are mixed is not critical, but it is convenient to add a solution containing the nickel or cobalt ions to a solution of the other reactants. The source of nickel or cobalt ions is usually a water-soluble nickel or cobalt salt, for example a sulphate, chloride or acetate.

Preferred solvents for use in the process are water and mixtures of water with water-miscible organic solvents, especially the water-miscible alcohols for example methanol, ethanol and isopropanol. In many instances the complex precipitates from the solution, so that it can be recovered by filtration of the reaction mixture. The proportion of the organic solvent in water/solvent mixtures and the volumes of solvents employed can then be adjusted to provide an optimum differential between the solubilities of the starting materials and the solubility of the product. Routine experimentation to establish such optimum conditions is within the capabilities of the person skilled in the art. In general, however, alcohol/water mixtures in which the ratio by volume is within the range 2:1 to 1:2 are satisfactory. Other water-miscible organic solvents can be used provided they are substantially chemically inert with respect to the other materials present, examples being glycols and tetrahydrofuran.

Formation of the complex normally occurs, with precipitation of the complex, when the reactants are mixed at room temperature. However, the temperature can be varied if desired; for example solutions of the reactants could be mixed at a temperature in the range 30° to 100° C., and the reaction mixture cooled to a temperature in the range 20° to $-10°$ C. to recover the product. In some circumstances, partial or complete evaporation of the solvent may be useful as a step in the isolation of the complex.

As regards the proportions of reactants used in the preparation of the complexes, it is preferred to employ substantially stoichiometrically equivalent amounts of the alkali metal salt of the organic thiosulphate and of the nickel or cobalt ions. Where the metal and the amine are known to form a definite complex cation, the amount of amine relative to the amount of nickel or cobalt employed will preferably be sufficient to form that cation. This amount is usually two or three gram-moles of amine per gram-atom of nickel or cobalt. If the association between the nickel or cobalt and the amine is indefinite, it is preferred to use at least 2 gram-moles, for example from 2 to 6 gram moles, of amine per gram atom of nickel or cobalt.

The exact proportions of reactants are not too critical in the process in instances where the complex precipitates from the solution, because excess reactants will remain in the solution after removal of the product by filtration.

The complexes of the invention are especially effective as rubber-metal adhesion promoters in compositions in which the rubber is cis-polyisoprene, either natural or synthetic, and in blends containing at least 25% by weight of cis-polyisoprene with other rubbers. Preferably the rubber, if a blend, contains at least 40% and more preferably at least 60% by weight of cis-polyisoprene. Examples of other rubbers which may be blended with cis-polyisoprene include poly-1,3-butadiene, copolymers of 1,3-butadiene with other monomers, for example styrene, acrylonitrile, isobutylene and methyl methacrylate, ethylenepropylene-diene terpolymers, and halogen-containing rubbers such as chlorobutyl, bromobutyl and chloroprene rubbers.

In the compositions of the invention the essential vulcanising agent is sulphur, but other vulcanising agents such as amine disulphides need not be excluded. The amount of sulphur in the compositions is typically from 2 to 6 parts by weight per 100 parts by weight of rubber, with a preferred range being from 2.5 to 4 parts per 100 parts by weight of rubber. An advantage of the adhesion promoters of the invention over the conventionally-used cobalt compounds is that they are effective at lower sulphur levels. The principal significance of this is that over the range of sulphur levels that gives vulcanisates of acceptable physical properties, those vulcanisates prepared using lower levels of sulphur show greater resistance to reversion and oxidative ageing than those prepared using higher levels of sulphur.

The preferred vulcanisation accelerators for use in the present invention are the benzothiazole-2-sulphenamides, for instance N-isopropyl-benzothiazole-2-sulphenamide, N-tert-butylbenzothiazole-2-sulphenamide, N-cyclohexylbenzothiazole-2-sulphenamide, N,N-dicyclohexylbenzothiazole-2-sulphenamide and 2(morpholinothio)benzothiazole. A single accelerator or a mixture of accelerators may be used. Best results are usually obtained using the benzothiazole-2-sulphenamides which have relatively long induction times, for example N,N-dicyclohexyl benzothiazole-2-sulphenamide and 2(morpholinothio)benzothiazole. In the compositions of the invention, these are usually used in amounts of from 0.3 to 2, preferably from 0.4 to 1.0 and more preferably from 0.5 to 0.8, parts by weight per 100 parts by weight of rubber.

The adhesion promoters defined above are very effective in promoting bonding between rubber and brass-coated steel. The brass typically has a copper content of from 60 to 70% by weight, with the optimum percentage depending on the particular conditions under which the bond is formed. The brass coating on brass-coated steel can have a thickness of, for example, from 0.07 to 0.7 micrometer. Rubber can also be bonded effectively to alloys of copper and zinc containing small amounts of one or more other metals, for example cobalt, nickel or iron.

Mixtures of different complexes of the above formula can be used as adhesion promoters in a composite of the invention. Moreover, it is possible to use a mixture of a complex of the present invention with one or more of the organic thiosulphates disclosed in No. EP-A-O 109 955.

The amount of adhesion promoter which, as indicated above, may be a single compound or a mixture, employed in the present invention is preferably from 0.5 to 4, for example from 1 to 3, parts by weight or rubber.

The adhesion promoters used in this invention can be incorporated into rubber by conventional mixing procedures, for example by adding them in a Banbury mixer or by adding them to the rubber on a mill. Ordinarily, with low melting solid additives, no special precautions are necessary for obtaining good dispersions. However, when using higher melting solids it is recommended that they be ground to a fine powder, preferably 70 micrometer particle size or less, to ensure adequate dispersion. In certain instances, it is convenient to add a solid adhesion promoter as a predispersion of particulate material in a rubber-compatible hydrocarbon oil or polymer, for example EPDM rubber.

Additives which are conventionally present in rubber compositions which are to be bonded to metal, are normally used in the vulcanisable compositions of the present invention. Such additives include carbon black, usually a carbon black of the N300 series such as N347 or N326, which typically is used in an amount of from 40 to 70 parts by weight per 100 parts by weight of rubber. Other such additives are, for example, zinc oxide, which may be used in an amount of, for instance, from 2 to 10 parts by weight per 100 parts by weight of rubber; stearic acid at a level of, for instance, from 0.5 to 2 parts by weight per 100 parts by weight of rubber; hydrocarbon softeners and extender oils; antidegradants, for example N-alkyl-N'-phenyl-p-phenylenediamines; and tackifiers. Other fillers may be used, for example silica, and the rubber stocks may also contain metal oxide activators other than zinc oxide, for example magnesium oxide, other bonding agents or promoters, for example phenolic, resorcinol and/or melamine adhesive resins, prevulcanisation inhibitors, for instance N-cyclohexylthiophthalimide, and corrosion inhibitors, for example inhibitors based on boric acid, organic borates, inorganic borates such as sodium tetraborate, inorganic phosphates and chromates. The metal surface to which the rubber is to be bonded can be subjected to various pre-treatments, for example to ensure complete cleanliness or to confer corrosion resistance.

The invention is illustrated by the following Examples:

EXAMPLE 1

This Example describes the preparation of a nickel/amine complex salt of hexane-1,6-bisthiosulphate.

Hexane-1,6-bisthiosulphate, disodium salt, dihydrate (HTSNa, 39 g, 0.1 mole) and 1,3-diamine-2,2-dimethylpropane (22.4 g, 0.2 mole) were dissolved in 2:1 water-/ethanol (300 ml), to form a solution to which was added dropwise at room temperature and with good stirring a solution of $NiCl_2.6H_2O$ (26.2 g, 0.11 mole) in water (50 ml). The pink precipitate was filtered and dried in vacuo at room temperature: yield 50 g.

The elemental analysis indicated that the product was substantially a dehydrated bis(diamine)nickel salt of hexamethylene-1,6-bisthiosulphate, containing 15% excess of nickel.

EXAMPLE 2

This Example described the preparation of the nickel-/ethylene diamine complex salt of hexane-1,6-bisthiosulphate. A solution of nickel acetate tetrahydrate (0.1 mole) in water (200 ml) was added dropwise with stirring at room temperature to a solution of hexane-1,6-bisthiosulphate, disodium salt, dihydrate (39 g, 0.1 mole) and ethylene diamine (15 g, 0.3 mole) in water (100 ml). The mixture was stirred for 10 minutes at room temperature, cooled to 0° C. and filtered. The precipitate was washed first with ethanol, then with ether, and was then dried. Yield, 47.2 g (theory 54.8 g) of a well crystallized red-violet compound.

The elemental analysis was correct for a tris(ethylenediamine)nickel salt of hexamethylene-1,6-bisthiosulphate.

EXAMPLE 3

In this Example, the metal is nickel and the complexing amine is N-tert-octyl-N-benzylamine.

A solution of nickel sulphate hexahydrate (26.3 g, 0.1 mole) in water (100 ml) was added dropwise with stirring at room temperature to a solution of hexane-1,6-bisthiosulphate, disodium salt, dihydrate (39 g, 0.1 mole) and N-tert-octyl-N-benzylamine (44 g, 0.2 mole) in a mixture of equal parts by volume of ethanol and water (200 ml). A green precipitate formed, and at the end of these additions, the suspension was filtered. The solid was washed with water and dried: yield 80.8 g.

Elemental analysis for C, H, N and S was consistent with a trihydrate of a nickel (bisamine) salt, but the nickel content was high.

EXAMPLE 4

In this Example, the metal is cobalt and the complexing amine is N-tert-octyl-N-benzylamine.

The procedure was similar to that of Example 3, using a solution of cobalt sulphate instead of nickel sulphate.

Elemental analysis of the product was consistent with it being essentially a dihydrate containing two molecules of the amine per cobalt atom.

EXAMPLE 5

In this Example, the metal is nickel and the complexing amine is a polyethyleneimine.

A solution of a polyethyleneimine having an average MW of 50,000 (13 g) in water (50 ml) was added dropwise with stirring at room temperature to a solution of nickel sulphate hexahydrate (26.3 g, 0.1 mol) and hexane-1,6-bisthiosulphate disodium salt, dihydrate (39 g, 0.1 mole) in water (100 ml). A violet solid was precipitated; the suspension was stirred for 1 hour and then filtered, and the solid which was collected was washed and then dried under vacuum: yield 63 g.

EXAMPLE 6

This Example describes the preparation of a nickel/amine complex salt of p-xylene bisthiosulphate.

p-xylylene bis(thiosulphate), disodium salt (132.5 g, 0.35 mole) was dissolved in a mixture of two parts by volume of water and one part by volume of ethanol (1 l) at 50° C. 1,3-Diamino-2,2-dimethylpropane (72.1 g, 0.7 mole) was added with stirring, followed by a solution of nickel sulphate hexahydrate (92.7 g, 0.35 mole) in water (300 ml). A solid was precipitated and the suspension was stirred for 30 minutes after the addition of the nickel sulphate was complete. The suspension was cooled and then filtered, and the solid thus collected was washed and dried: yield 162 g (78%).

Elemental analysis: Found: C, 33,48; H, 6.04; N, 8.93; S, 18.91; O, 20.70; Ni, 8.56; Na, 1.29. Calculated for $C_{18}H_{36}N_4S_4O_6Ni, 2H_2O$: C, 34.45; H, 6.42; N, 8.93; S, 20.43; O, 20.40; Ni, 9.36.

EXAMPLE 7

This Example describes the preparation of a nickel/amine complex salt, with the formation of the required intermediate alkali metal bisthiosulphate in situ.

A mixture of 1,2-dibromoethane (18.8 g, 0.1 mole) and sodium thiosulphate pentahydrate (49.6 g, 0.2 mole) in a solvent consisting of equal parts by volume of ethanol and water (200 ml) was refluxed for 1 hour. The solvent was then evaporated and the dry residue was dissolved in a mixture of 3 parts by volume of water and 1 part by volume of ethanol (200 ml). To this solution at room temperature, 1,3-diamino-2,2-dimethylpropane (20.4 g, 0.2 mole) was added with stirring, followed by the dropwise addition of a solution of nickel sulphate hexahydrate (26.3 g, 0.1 mole) in water (45 ml). The resulting suspension was filtered, and the solid on the filter was washed with water and dried under vacuum at 25° C.: yield 44 g (90%).

Elemental analysis: Found: C, 25.27; H, 5.78; N, 9.71; S, 22.52; O, 22.25; Ni, 10.05; Na, 1.45. Calculated for $C_{12}H_{32}N_4S_4O_6Ni, 1.5H_2O$ C, 26.56; H, 6.50; N, 10.32; S, 23.64; Ni, 10.82.

EXAMPLE 8

This Example describes the preparation of a nickel/amine complex salt of but-2-ene-1,4-bisthiosulphate.

A solution of nickel chloride hexahydrate (26.2 g, 0.11 mole) in water (50 ml) was added dropwise, during a period of 30 minutes, to a stirred solution of the disodium salt of but-2-ene-1,4-bisthiosulphate (0.1 mole), and 1,3-diamino-2,2-dimethylpropane (22.4 g, 0.22 mole) in water (200 ml) and ethanol (100 ml) at room temperature. The mixture was stirred at room temperature for a further 30 minutes after the addition was complete, and was then filtered. The yield of solid collected was 45.0 (83%).

Elemental analysis: Found: C, 29.32; H, 6.26; N, 9.61; S, 21.96; O, 22.00; Ni, 10.08; Na, 0.10. Calculated for $C_{14}H_{34}N_4S_4O_6Ni, 2H_2O$ C, 29.12; H, 6.63; N, 9.70; S, 22.21; O, 22.16; Ni, 10.16.

EXAMPLE 9

This Example describes the preparation of the nickel/ethylenediamine complex salt of but-2-ene-1,4-bisthiosulphate.

A solution of 99% pure nickel acetate tetrahydrate (11.3 g, 0.045 mole) in water (70 ml) was added dropwise to a stirred solution of the disodium salt of but-2-ene-1,4-bisthiosulphate (0.045 mole) and 99% pure ethylenediamine (8.2 g, 0.135 mole) in water (40 ml) at room temperature. Stirring was continued at room temperature for a further 30 minutes and the solution was then cooled to 0° C. No precipitation occurred, so the solution was then evaporated to dryness under vacuum. Water (36 ml) at 0° C. was added to the residue and the mixture was filtered rapidly. The solid thus collected was washed with ethanol: yield 22.6 g (97%). It was recrystallised from aqueous ethanol. Elemental analysis of the recrystallised material gave the following result:

Found: C, 23.32; H, 5.76; N, 16.15; S, 24.59; Ni, 11.36. Calculated for $C_{10}H_{30}N_6S_4O_6Ni$: C, 23.22; H, 5.85; N, 16.25; S, 24.79; Ni, 11.35.

EXAMPLE 10

This Example describes the preparation of the nickel/1,3-diaminopropane complex of hexane-1,6-bisthiosulphate.

98% pure 1,3-diaminopropane (11.35 g, 0.15 mole) was added dropwise to a stirred solution of the disodium salt of hexane-1,6-bisthiosulphate (0.05 mole) in water (90 ml) and ethanol (45 ml) at 35° C. This was followed by the dropwise addition of a solution of nickel sulphate hexahydrate (13.15 g, 0.05 mole) in water (20 ml). The mixture was stirred for 30 minutes at room temperature, during which period precipitation of a solid occurred. After cooling to 0° C., the mixture was filtered and the solid thus collected was dried under vacuum: Yield 25.1 g (85%). Examples 11, 12 and 13 describe the preparation of nickel/amine complexes with a monothiosulphate anion.

EXAMPLE 11

A solution of nickel sulphate hexahydrate (6.6 g, 0.025 mole) in water (25 ml) was added with stirring to a solution of sodium n-dodecylthiosulphate (15.2 g, 0.05 mole) and N-benzyl-N-1,1,3,3-tetramethylbutylamine (11.0 g, 0.05 mole) in water/ethanol (100 ml/100 ml). The mixture was stirred at room temperature for 30 minutes, then cooled to 0° C. and filtered. The solid collected was washed with water and then dried under vacuum. Yield 25.6 g (theory 26.5 g) of a pale green solid. Elemental analysis gave the following result:

C, 57.33; H, 8.83; S, 11.10; O, 13.50; N, 2.42; Ni, 5.81. Calculated for a nickel bis(amine) complex with 3.5 moles $H_2O$: C, 57.73; H, 9.60; S, 11,42; O, 13.53; N, 2,49; Ni, 5.23.

EXAMPLE 12

A solution of nickel sulphate hexahydrate (13.2 g, 0.05 mole) in water (50 ml) was added with stirring to a solution of sodium n-dodecylthiosulphate (30.4 g, 0.1 mole) and ethylene diamine (9.0 g, 0.15 mole) in water- /ethanol (200 ml/100 ml). The mixture was stirred at room temperature for 30 minutes, then cooled to 0° C. and filtered. The solid collected was washed with water and dried under vacuum. Yield 34.5 g (theory 40.1 g) of a violet solid.

Elemental analysis: Found: C, 45.74; H, 8.94; S, 15.63; O, 12.01; N, 10.20; Ni, 7.08. Calculated for an anhydrous nickel tris(amine) complex C, 44.93; H, 9.30; S, 15.99; O, 11.97; N, 10.48; Ni, 7.32.

EXAMPLE 13

A solution of nickel sulphate hexahydrate (13.2 g, 0.05 mole) in water (50 ml) was added with stirring to a solution of sodium n-dodecylthiosulphate (30.4 g, 0.1 mole) and 1,3-diaminopropane (11.1 g, 0.15 mole) in water/ethanol (200 ml/100 ml). The mixture was stirred at room temperature for 30 minutes, cooled to 0° C. and then filtered. The solid thus collected was washed with water and dried under vacuum. Yield 35.3 g (theory 42.2 g) of a violet solid.

Elemental analysis: Found: C, 44.83; H, 8.74; S, 15.78; O, 15.91; N, 6.87; Ni, 7.15. Calculated for a bis(amine) complex dihydrate C, 44.71; H, 9.26; S, 15.91; O, 15.88; N, 6.95; Ni, 7.28.

EXAMPLE 14

A solution of 1,3,5-triacryloylhexahydrotriazine (33 g) in water (250 ml) and ethanol (250 ml) was adjusted to pH 7 with sodium carbonate, sodium thiosulphate pentahydrate (100 g) was added, and the solution was refluxed for 3 hours, with the pH maintained at 6–8 by the addition of acetic acid. To the cooled solution was added a solution of nickel acetate tetrahydrate (49.6 g) dissolved in water (200 ml) and ethylene diamine (36 g). The mixture was stirred for 15 minutes at room temperature, the violet precipitate was collected by filtration, washed with water, then with ethanol, and dried to yield the product (54.9 g).

EXAMPLE 15

Evaluation of the adhesion promoters was carried out using a vulcanisable rubber composition of a type known as "skimstock" as follows:

|  | Parts by weight |
| --- | --- |
| Natural rubber | 100 |
| N 347 carbon black | 55 |
| Zinc Oxide | 8 |
| Stearic Acid | 2 |
| Process Oil | 3 |
| Tackifier | 3 |
| Antiozonant[1] | 2 |
| Antioxidant[2] | 1 |
| Sulphur | 4 |
| Accelerator[3] | 0.7 |
| Bonding promoter | see table below |

[1]N—1,3-dimethylbutyl-N'—phenyl-p-phenylenediamine
[2]Polymerised 2,2,4-trimethyl-1,2-dihydroquinoline
[3]2(morpholinothio)benzothiazole with the promoters of Examples 2, 3, 4, 6, 7 and 14. N,N—dicyclohexylbenzothiazole-2-sulphenamide with the promoters of Examples 8, 9 and 10.

Mixing of the ingredients except sulphur and accelerator was done in a laboratory scale Banbury mixer having a capacity of 1.57 liter and operating at a filling factor of about 0.8 and a rotor speed of 117 r.p.m., according to the following schedule:

| Time (mins.) | |
| --- | --- |
| 0 | Rubber placed in mixer and rotors started. |
| 1 | Half carbon black and zinc oxide added. |
| 2.5 | Remainder of carbon black, stearic acid, process oil, tackifier, antiozonant, antioxidant, bonding promoter added. |
| 4 | Sweep. |
| 5 | Dumped at temperature 150+ 5° C. |

The batch was then transferred to a mill at 70°–75° C. for sheeting off. Sulphur and accelerator were added to portions of the masterbatch on a mill as required.

The metal component was a typical brass-coated steel tyre cord having the construction 3+9+15×0.175+1, each cord having a coating of brass, approximately 0.20 micrometer thick, with an average copper content of 63.5% by weight.

Rubber/metal bond strengths were measured using the adhesion test described by R. C. Ayerst and E. R. Rodger, Rubber Chem. Technol. 45, 1497(1972). In this method, adhesion blocks are prepared in a similar manner to that specified in ASTM D-2229, but using clamping plates to hold the cords in the mould to maintain alignment during cure, and a frame for pre-loading and uniformly stressing the cord before mould building. The adhesion block comprises a strip of rubber having one end each of several uniformly-spaced lengths of cord embedded in one edge of the strip, and a similar array of lengths of cord, each length having one end embedded in the edge of the strip opposite the first edge and in staggered relationship to the cords in the first edge. Pullout adhesion is measured on a tensile tester by arranging the adhesion block so that the cords are vertical and the rubber strip horizontal, and by holding two lower wires and pulling out the upper wire between them at a crosshead speed of 5 cm/min. The pullout force recorded is the mean of the values for each of the several upper cords except those at each end of the strip, which are not taken into account in order to eliminate possible end effects. Where the pullout force exceeds the breaking load of one or more of the wires in the test procedure, this is signified in the Tables by the symbol >.

The results given in the tables below under the headings "Initial Adhesion", "Steam Ageing" and "Salt Bath Ageing" were obtained in adhesion blocks where the rubber was cured at 145° C. for $T_{90}+5$ minutes, "$T_{90}$" being the time in minutes taken for a sample of the same rubber cured in a rheometer (I.S.O. 3417-1977 (E)) to reach 90% of the maximum modulus. Blocks that were "steam aged" were kept in steam under pressure at 120° C. for 8 hours and those that were "salt bath aged" were immersed in a 5% sodium chloride solution at 90° C. for 48 hours after curing and before testing.

In "Steel Cord: Analysis of Used Truck Tires and Simulation of the Found Phenomena in Laboratory Experiments" an article in "Tire Reinforcement and Tire Performance", ASTM STP 694, R. A. Fleming and D. I. Livingston, Eds, American Society for Testing and Materials, 1979, pp 69–86, C. C. J. de Jong concludes that in evaluating tyres and other composites containing metal and cord reinforcement, attention should be paid to aged adhesion rather than to initial adhesion. The ageing conditions mentioned above are similar to those proposed by de Jong to simulate, at an enhanced level, various conditions which might be encountered during the service life of a tyre.

The results obtained are set out in the following table. The value of the complexes of the invention as rubber/metal adhesion promoters, especially in improving the resistance of the bond to salt bath ageing, is apparent.

| Promoter Example No. | Amount phr | Pull-out force in Newtons/cm | | |
|---|---|---|---|---|
| | | Initial Adhesion | Steam Ageing | Salt Bath Ageing |
| Control | None | 470 | — | 230 |
| 2 | 1.2 | 470 | — | 270 |
| 3 | 1.4 | 470 | — | 290 |
| 4 | 1.4 | 480 | — | 440 |
| 6 | 1.2 | 470 | — | 350 |
| 7 | 1.2 | 450 | — | 320 |
| 14 | 2.5 | 480 | — | 370 |
| Control | None | 380 | 450 | 260 |
| 8 | 1.5 | 490 | >484 | 450 |
| 9 | 1.5 | 450 | >500 | 300 |
| 10 | 1.6 | 490 | >450 | 420 |

We claim:

1. A composite comprising a sulphur-vulcanisable rubber composition containing the rubber, sulphur, a vulcanisation accelerator and a rubber/metal adhesion promoter, and a component having a metal surface in contact with the composition, characterised in that the rubber/metal adhesion promoter comprises a complex containing an organic thiosulphate anion and cationic nickel or cobalt in association with an amine.

2. A composite according to claim 1, in which the metal surface is a brass surface, and in the complex, the organic thiosulphate anion has the formula $R^2(S_2O_3^-)_x$ where $R^2$ is an organic radical of valency x and x has a value of 1, 2 or 3.

3. A composite according to claim 2, in which in the complex, x has the value 1 and $R^2$ is an alkyl or alkenyl group containing up to 20 carbon atoms or is a benzyl or alkylbenzyl group.

4. A composite according to claim 3, in which, in the complex, R is an alkyl group containing from 4 to 16 carbon atoms.

5. A composite according to claim 2 in which, in the complex, x has the value 2 and $R^2$ is an alkylene group containing 2 or from 5 to 16 carbon atoms, an analogous group containing from 4 to 16 carbon atoms and one or more double or triple bonds, or a xylylene group.

6. A composite according to claim 5 in which, in the complex, $R^2$ is an alkylene group containing 2 or from 5 to 16 carbon atoms, an alkenylene group containing from 4 to 16 carbon atoms, or a 1,3- or 1,4-xylylene group.

7. A composite according to claim 2, in which, in the complex, $R^2$ is a tri-N-substituted hexahydrotriazine where the substituent on each nitrogen atom is a group having the formula —$COC_mH_{2m}$— where m has a value of from 1 to 6.

8. A composite according to claim 2, in which, in the complex, the amine is (A) an amine having the general formula $H_2N$—R—$NH_2$ where R represents (i) a straight- or branched-chain group $C_nH_{2n}$, n having a value of from 2 to 8, with the amine groups being separated by a sequence of no more than 3 carbon atoms, (ii) 1-phenylethylene or 1,2-diphenylethylene, or (iii) —$CH_2CH_2NHCH_2CH_2$—, (B) 2,2-bipyridyl, (C) an N-benzyl-N-(tert-alkyl)amine where the tert-alkyl group has the formula

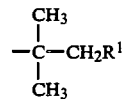

where $R^1$ represents H or a straight- or branched-chain alkyl group of from 1 to 8 carbon atoms, or (D) a poly(ethyleneimine).

9. A composite according to claim 8, in which, in the complex, the amine is 1,2-diaminoethane, 1,3-diaminopropane, 1,2-diamino-2-methylpropane, 1,3-diamino-2,2-dimethylpropane, N-benzyl-N-t-butylamine or N-benzyl-N-t-octylamine.

10. A composite according to claim 1 in which the diene rubber is natural or synthetic cis-polyisoprene or a blend of rubbers containing at least 25% by weight of cis-polyisoprene.

11. A composite according to claim 1 in which the amount of adhesion promoter is from 0.5 to 4 parts by weight per 100 parts by weight of rubber.

12. A composite according to claim 1 in which the amount of sulphur is from 2 to 6 parts by weight per 100 parts by weight of rubber.

13. A composite according to claim 1 containing a benzothiazole-2-sulphenamide as vulcanisation accelerator.

14. An article in which a vulcanised rubber component is bonded to a metal surface, the article having been obtained by heating a composite according to claim 1 to a vulcanisation temperature to vulcanise the rubber.

* * * * *